United States Patent [19]

Jones et al.

[11] 4,154,586
[45] May 15, 1979

[54] RESPIRATOR CARTRIDGE END-OF-SERVICE LIFT INDICATOR SYSTEM AND METHOD OF MAKING

[75] Inventors: John A. Jones, Wilbraham, Mass.; Adolfo V. Ayes, Hartford, Conn.

[73] Assignee: American Optical Corporation, Southbridge, Mass.

[21] Appl. No.: 869,191

[22] Filed: Jan. 13, 1978

[51] Int. Cl.$^2$ .................... B01D 51/10; B01D 53/04; G01N 31/10; G01N 31/22
[52] U.S. Cl. .................... 55/274 BN; 55/DIG. 33; 55/DIG. 34; 252/186; 252/458; 252/467; 422/86; 422/120
[58] Field of Search ................ 23/252 R, 284, 232 R, 23/254 R; 55/274, 275, DIG. 33, DIG. 34, DIG. 35; 252/408, 186, 188, 436, 458

[56] References Cited

U.S. PATENT DOCUMENTS

| | | | |
|---|---|---|---|
| 2,231,181 | 2/1941 | Brooks | 252/436 X |
| 3,223,488 | 12/1965 | Luckey | 23/254 R |
| 3,350,175 | 10/1967 | McConnaughey et al. | 23/254 X |
| 3,489,507 | 1/1970 | Gardner et al. | 23/252 R |
| 3,511,596 | 5/1970 | Adler et al. | 252/436 X |
| 3,966,440 | 6/1976 | Roberts | 23/254 R X |
| 4,043,934 | 8/1977 | Shuler et al. | 55/387 X |

*Primary Examiner*—Joseph Scovronek
*Attorney, Agent, or Firm*—Jeremiah J. Duggan; Howard R. Berkenstock, Jr.; Alan H. Spencer

[57] ABSTRACT

Providing visual means for indicating when vapor/gas respirator cartridges have exhausted their capacity to provide respiratory protection at or below a hazardous concentration level. In combination with a vapor/gas indicator adapted to undergo a change in color with contact by an organic vapor or gas, there is provided a catalytic agent for enhancing activation and reaction of the indicator agent.

6 Claims, 2 Drawing Figures

RESPIRATOR CARTRIDGE END-OF-SERVICE LIFT INDICATOR SYSTEM AND METHOD OF MAKING

BACKGROUND OF THE INVENTION

1. Field of the Invention

This invention relates to respirator cartridges with particular reference to improvements in means and method for indicating end-of-service life of organic vapor/gas respirator cartridges.

2. Discussion of the Prior Art

Respirators of the type employing replaceable filter cartridges are commonly used for protection against a wide range of respiratory hazards which include toxic and disease producing dusts, mists, sprays, fumes, vapors and gases. The cartridges are replaced when their capacity to provide respiratory protection at or below hazardous concentration levels becomes apparent to the user or is otherwise arbitrarily or administratively determined.

Detection of cartridge exhaustion by a user's taste or smell of potentially hazardous fumes or gases coming through the cartridge or a resistance to his normal breathing due to clogging with dust may provide adequate protection against the danger of using spent cartridges in cases where the respiratory hazards are, for example, ammonia fumes, acidic and alkaline gases or certain dusts which produce odors, tastes and/or breathing resistances which are detectable before reaching hazardous concentrations.

Protection against organic vapors or gases which have no such warning properties, however, presents a much more serious problem which heretofore has required administrative control of cartridge use, i.e. its time of replacement being determined according to type and degree of toxicity of the hazard, its immediate concentration, the humidity at the sight and corollary environmental conditions. Variations in one or more of the aforesaid factors and their corrollaries during use of a particular cartridge can cause serious problems if not detected and, least of all, complicate end-of-service life calculations.

There are in the art a number of windowed respiratory cartridges or cannisters having color changing indicator means therewithin which allegedly afford indication of residual useful life and/or impending exhausting of the cartridges or cannisters. U.S. Pat. Nos. 1,537,519 and 3,966,440 are exemplary. These devices, however, involve the use of indicators supported by thin and/or opaque carriers such as strips of paper, activated alumina or the cartridge sorbent itself so that only the portion of the indicator against the window is visible.

The use of a porous translucent carrier for cartridge end-of-service life indicators which permits viewing thereinto for perception of a substantial depth of an indicator has been suggested in an application for patent filed January 5, 1977 and having Ser. No. 757,105, now abandoned.

While this provides an important advance in the art, i.e. by affording a more readily visible and reliable cartridge end-of-service life indication, there remains a need for still greater sensitivity to cartridge sorbent exhaustion, i.e. a more dramatic or vivid display of end-of-service life indication.

Accordingly, a principal object of this invention is to afford novel means and method for enhancing the color changing activity and general display function of gas oxidizable color indicators used in windowed or otherwise transparent respirator cartridges.

A corollary object is to enhance oxidation and color change of end-of-service life indicating means by catalytic action and/or preconditioning of vapors and gases reaching the indicating means.

Other objects and advantages of the invention will become more readily apparent from the following description.

SUMMARY OF THE INVENTION

In a gas/vapor sorbent-containing respirator cannister or cartridge having window means and a toxic gas/vapor oxidizable end-of-service life color indicator visible therethrough, the present invention includes an upstream catalytic/oxidizing agent for enhancing action of the color indicator. The agent is so positioned and formulated as to receive and oxidize a vapor or gas into a product more readily detected by the cartridge indicator and/or to so activate the gas or vapor that it can be more easily oxidized and detected by the indicator.

It is to be understood that the aforesaid window means may include any portion or all of the cartridge shell, the cartridge sorbent may comprise activated charcoal or other conventional means and use of the expression catalyst herein is to be interpreted in its broadest sense as meaning a substance that initiates a reaction enabling procedure under milder conditions than otherwise possible.

Details of the invention will become more readily apparent from the following description when taken in conjunction with the accompanying drawings in which.

DESCRIPTION OF THE PREFERRED EMBODIMENTS

Figure 1:
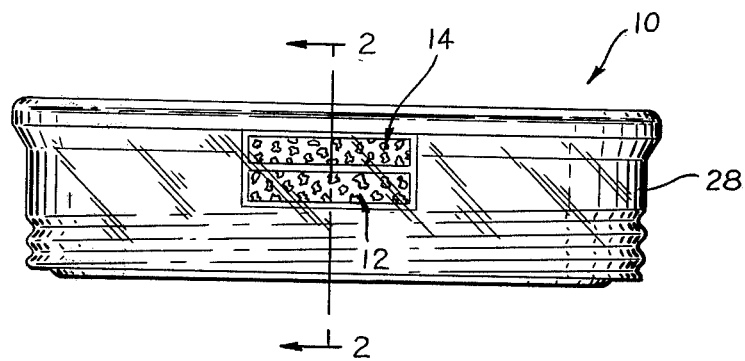
FIG. 1 is a side elevational view of an organic vapor/gas respirator cartridge having a transparent shell and embodying an end-of-service life indicator system according to the invention.

According to the invention there is provided in a transparent organic vapor/gas respirator cartridge 10 having an end-of-service life indicator 12 and a catalytic oxidizing agent, hereinafter referred to as catalyst 14, located adjacent indicator 12 in a position upstream thereof. As indicated by arrows 16 (FIG. 2) the stream of air and gases and/or vapors through cartridge 10 when in use passes into and through its perforated end 18, sorbent 20 and outwardly of perforated end 22. Thus, with indicator 12 and catalyst 14 supported in a compartmented perforated container 24, the portion of airstream 16 adjacent container 24 is caused to first enter catalyst 14 and then pass into indicator 12 prior to proceeding downstream through end 22 as illustrated with arrow 26.

Figure 2:
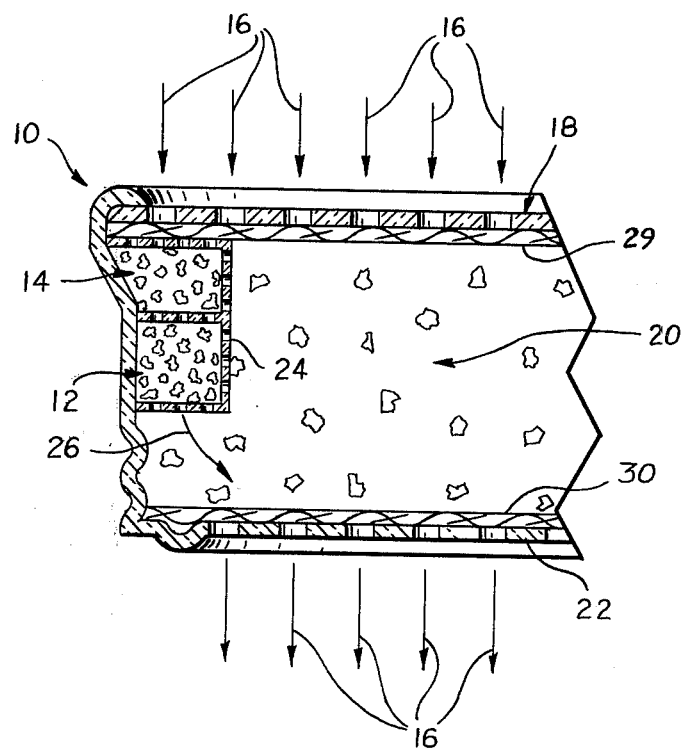
FIG. 2 is an enlarged fragmentary cross-sectional view of the cartridge taken generally along line 2—2 of FIG. 1.

It is to be understood that the construction of cartridge 10 as depicted in FIGS. 1 and 2 has been selected for purposes of illustrating principles of the invention only and that various other forms of respirator cartridge and/or cannister designs and constructions may be used within the scope of the invention. For example, cartridge 10 including the illustrated transparent shell 28 and perforated end covers 18 and 22 may be formed of metal such as aluminum or opaque plastic materials and provided with transparent window means for visual perception of indicator 12. Such window means having been illustrated in copending application Ser. NO. 757,105 will not be shown or further described herein. The cartridge sorbent 20, e.g. activated charcoal, is prevented from escaping through perforations in end covers 18 and 22 by liners 29 and 30 of felt, woven fabric or suitable screening.

Catalyst 14 is fabricated as follows:

(1) Measure 50 grams of granular petroleum base activated carbon.

(2) Prepare impregnating solution: a. 200 ml $H_2O$ (distilled)

b. add 30 ($\pm$20) grams $Na_2CR_2O_7$ and dissolve c. add 30 (+32, −15) ml of reagent or technical grade concentrated $H_2SO_4$ and allow to cool.

(3) Pour carbon into solution (2) and permit to stand for sufficient time to accomplish total saturation, e.g. one hour.

(4) Decant remaining liquid from carbon and allow carbon to dry, e.g. 3 hours at a temperature of from 150° F. to 250° F. in an air-circulating oven.

Note: The carbon reduces the impregnating solution and functions as its carrier.

Modifications of the foregoing fabrication procedure are:

A. Delete (c) in step (2) and proceed to step (3).

B. Delete (c) in step (2) and add 30 ($\pm$5) grams $FeCl_3$ and proceed to step (3).

C. In (b) of step (2) use approximately 10 grams $Na_2CR_2O_7$, in (c) of step (2) use approximately 10 ml $H_2SO_4$ and add 10($\pm$5) grams $FeCl_3$ and 5 ($\pm$2) grams ZnO. Mix the foregoing in any order but with $H_2SO_4$ added last.

D. Add 40 ($\pm$20) ml of commercial grade granular silica gel to the sodium dichromate decantate of step (4), this is reduced sodium dichromate. Permit the silica gel to stand in the reduced sodium dichromate solution for a period of time sufficient to accomplish total saturation.

One hour will produce satisfactory results.

Decant excess liquid from the silica gel and dry, e.g. two to four hours at from 150° F. to 250° F. Three hours at 225° F. has demonstrated desirable results.

With one or another of the foregoing reduced sodium chromate catalysts carried by either the activated carbon or silica gel and placed upstream of indicator 12 as illustrated, enhanced activation and intensification of the display of color of indicator 12 is accomplished for improved end-of-service life indication.

A desirable indicator 12 may consist of a solution of a reagent grade sodium dichromate in sulfuric acid and water supported by granular silica gel. The solution is added to the silica gel and dried in place. Those interested in details of such indicators may refer to copending U.S. Application Serial No. 757,105.

It should be apparent from the foregoing that the indicator system of the present invention is readily adaptable to various types and/or forms of respirator cartridges or cannisters other than that illustrated in the present drawings. Various modifications and adaptations of the precise mechanical and chemical forms of the invention here shown and described may be made to suit particular requirements, e.g. agents other than the above-described activated carbon may be used to reduce the sodium dichromate solution. Formaldehyde and hydrogen peroxide are examples. The foregoing illustrations are not to be interpreted as restrictive of the invention beyond that necessitated by the following claims.

We claim:

1. In a respirator cartridge having a shell within which there is supported a gas/vapor sorbent and an indicator agent selected from the group consisting of sodium dichromate and potassium dichromate characterized to undergo a change in color concomitant with exposure to concentrations of organic vapors and gases which are below a threshold limit known to be safe to inhale, the improvement comprising:

catalytic/oxidizing means for rendering a gas/vapor entering the cartridge and passing through said means more readily detected by said indicator agent than with non-use of said means, said catalytic/oxidizing means being located adjacent to an upstream of said indicator agent in said cartridge.

2. The improvement according to claim 1 wherein said catalytic/oxidizing means includes a carrier.

3. The improvement according to claim 2 wherein said carrier is activated carbon.

4. The improvement according to claim 2 wherein said carrier is silica gel.

5. The improvement according to claim 1 wherein said catalytic/oxidizing means is formulated of the approximate related proportions of ingredients of 50 grams activated carbon to which is added an impregnating solution of 200 ml $H_2O$, 30 ($\pm$20) grams $Na_2Cr_2O_7$ and 30 (+30, −15) ml concentrated $H_2SO_4$;

said solution being reduced by said carbon and excess thereof decanted from said carbon with the residue allowed to dry in place as said catalytic/oxidizing means.

6. The improvement according to claim 5 wherein said decanted reduced sodium dichromate solution is applied to granular silica gel and dried thereinplace to provide said catalytic/oxidizing means.

* * * * *

UNITED STATES PATENT AND TRADEMARK OFFICE
CERTIFICATE OF CORRECTION

PATENT NO. : 4,154,586
DATED : May 15, 1979
INVENTOR(S) : John A. Jones and Adolfo V. Ayes It is certified that error appears in the above-identified patent and that said Letters Patent are hereby corrected as shown below:

Change the title from "Respirator Cartridge End-of-Service Lift Indicator System and Method of Making" to --Respirator Cartridge End-of-Service Life Indicator System and Method of Making--.

Signed and Sealed this

Eighteenth Day of September 1979

[SEAL]

Attest:

Attesting Officer

LUTRELLE F. PARKER
Acting Commissioner of Patents and Trademarks